United States Patent
Pugh et al.

(10) Patent No.: US 9,915,829 B2
(45) Date of Patent: Mar. 13, 2018

(54) METHOD OF MANUFACTURING AN OPHTHALMIC LENS WITH A PASSIVE EVENT-BASED COLORATION SYSTEM

(71) Applicant: Johnson & Johnson Vision Care, Inc., Jacksonville, FL (US)

(72) Inventors: Randall B. Pugh, Jacksonville, FL (US); Karson S. Putt, Jacksonville, FL (US); Camille Higham, Jacksonville, FL (US); Sharika Snook, St. Augustine, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 683 days.

(21) Appl. No.: 13/899,528

(22) Filed: May 21, 2013

(65) Prior Publication Data

US 2014/0346695 A1 Nov. 27, 2014

(51) Int. Cl.
*G02C 7/04* (2006.01)
*A61B 3/10* (2006.01)
(Continued)

(52) U.S. Cl.
CPC .............. *G02C 7/049* (2013.01); *A61B 3/101* (2013.01); *A61B 5/14507* (2013.01);
(Continued)

(58) Field of Classification Search
CPC ... A61B 5/14507; A61B 5/6821; A61B 3/101; A61B 5/14532; A61B 5/1455; A61B 5/145; A61B 3/0008; A61B 3/0025; A61B 3/0058; A61B 3/066; A61B 3/103; A61B 3/113; A61B 3/185; A61B 5/0017; A61B 5/002; A61B 5/0059; A61B 5/0071; A61B 5/0488; A61B 5/04888; A61B 5/1103; A61B 5/165; A61B 5/412; A61B 5/4836; A61B 5/723; G02C 7/04; G02C 11/10;
(Continued)

(56) References Cited

U.S. PATENT DOCUMENTS 7,809,417 B2 * 10/2010 Abreu .................. A61B 3/1241
600/318
2010/0072643 A1 * 3/2010 Pugh et al. .................... 264/2.7
(Continued)

FOREIGN PATENT DOCUMENTS

DE 102006005652 A1 9/2007
WO WO 2000025662 A1 5/2000
(Continued)

OTHER PUBLICATIONS

Subbaraman, L.; Jones, L.; What Influences Contact Len-Related Dry Eye, Contact Lens Spectrum, Jul. 1, 2009.*
(Continued)

*Primary Examiner* — Jeffrey M Wollschlager
*Assistant Examiner* — Armand Melendez (57) ABSTRACT

The present invention discloses methods and apparatus for methods and apparatus for manufacturing an Ophthalmic Lens with passive event coloration mechanisms, which may not require a power source. In some embodiments, the passive event coloration mechanisms may be combined with Rigid Inserts or Media Inserts, wherein the inserts may provide additional functionalities.

20 Claims, 6 Drawing Sheets

(51) Int. Cl.
  *G02C 7/02* (2006.01)
  *A61B 5/00* (2006.01)
  *A61B 5/145* (2006.01)
  *B29L 11/00* (2006.01)

(52) U.S. Cl.
  CPC .......... *A61B 5/6821* (2013.01); *A61B 5/7445* (2013.01); *G02C 7/021* (2013.01); *G02C 7/04* (2013.01); *A61B 5/14532* (2013.01); *A61B 5/14546* (2013.01); *B29L 2011/0041* (2013.01); *G02C 7/046* (2013.01)

(58) Field of Classification Search
  CPC ........ G02C 7/021; G02C 7/046; G02C 7/101; G02C 7/022; G02C 7/02; G02C 7/048; G02C 7/10; G02C 7/12; G02C 7/049; G02C 7/083; G02C 7/085; G02C 7/102; G02C 7/104; G02C 7/105; G02C 7/06; G02C 7/08; G02C 7/108; G02C 7/027; G02C 7/028; G02C 7/041; G02C 7/043; G02C 7/044; G02C 7/086; G02C 2202/16; G02C 2202/04; G02C 2202/06; G02C 2202/08; G02C 2202/12; G02C 2202/18; G02C 2202/20; G02C 2202/22; G02C 11/00; G02C 11/04; G02C 5/001; G02B 1/043; G02B 26/005; G02B 3/14; G02B 1/00; G02B 27/017; G02B 27/0172; G02B 5/30; B29D 11/00038; B29D 11/00807; B29D 11/0817; B29D 11/00826; B29D 11/00125; B29D 11/00009; B29D 11/00048; B29D 11/00028; B29D 11/00346; B29D 11/00903; B29D 11/00019; B29D 11/00057; B29D 11/00067; B29D 11/00076; B29D 11/00134; B29D 11/00144; B29D 11/00153; B29D 11/0025; B29D 11/00317; B29D 11/00461; B29D 11/00634; B29D 11/00865; B29D 11/00894; B29D 11/00932; A61F 2/1624; A61F 2/0017; A61F 2/16; A61F 2/1627; A61F 2/1648; A61F 2002/482; A61F 2220/005; A61F 2230/0004; A61F 2250/0043; A61F 2/14; A61F 2/1635
  USPC .......................................... 261/127
  See application file for complete search history.

(56) References Cited

U.S. PATENT DOCUMENTS

| | | | |
|---|---|---|---|
| 2010/0110372 A1* | 5/2010 | Pugh et al. | 351/177 |
| 2010/0113901 A1* | 5/2010 | Zhang et al. | 600/319 |
| 2011/0136929 A1* | 6/2011 | Chow | A61B 5/14532 521/105 |
| 2011/0157544 A1* | 6/2011 | Pugh et al. | 351/158 |
| 2011/0249235 A1* | 10/2011 | Duis | B29D 11/00048 351/159.33 |
| 2012/0113384 A1* | 5/2012 | Pasternak et al. | 351/159.3 |

FOREIGN PATENT DOCUMENTS

| | | | | |
|---|---|---|---|---|
| WO | WO0203855 | * | 1/2002 | A61B 5/00 |
| WO | WO2004064629 | * | 1/2004 | A61B 5/00 |
| WO | WO 2011010267 A1 | | 1/2011 | |
| WO | WO 2013049000 A1 | | 4/2013 | |

OTHER PUBLICATIONS

PCT Search Report for Corresponding Application No. PCT US2014 038725 dated Aug. 8, 2014 Date of Completion Jul. 30, 2014.

* cited by examiner

METHOD OF MANUFACTURING AN OPHTHALMIC LENS WITH A PASSIVE EVENT-BASED COLORATION SYSTEM

FIELD OF USE

This invention describes methods, apparatus, and devices related to Ophthalmic Lenses with an event coloration mechanism, wherein the event coloration mechanism may provide a visual indication upon the occurrence of a predefined event. More specifically, the invention describes the method of manufacturing Ophthalmic Lenses with event coloration mechanisms that may not require a power source.

BACKGROUND

Traditionally, an Ophthalmic Device, such as a contact lens, an intraocular lens, or a punctal plug included a biocompatible device with a corrective, cosmetic, or therapeutic quality. A contact lens, for example, can provide one or more of vision correcting functionality, cosmetic enhancement, and therapeutic effects. Each function is provided by a physical characteristic of the lens. A design incorporating a refractive quality into a lens can provide a vision corrective function. A pigment incorporated into the lens can provide a cosmetic enhancement. An active agent incorporated into a lens can provide a therapeutic functionality. Such physical characteristics may be accomplished without the lens entering into an energized state.

The functionality of the Ophthalmic Lens may not be limited to ophthalmic functions. When placed on an eye, an Ophthalmic Lens is in contact with the ocular environment, such as, tear fluid, which may include constituents similar to those contained in blood. Accordingly, an Ophthalmic Lens may provide a platform to monitor specific attributes of the ocular environment, such as tear fluid constituents.

It may be desirable to improve the process, methods, and resulting devices for realizing event coloration mechanisms of various kinds. It may be anticipated that some of the solutions for passive event coloration mechanisms inserts may provide novel aspects for energized devices and other biomedical devices. Accordingly, novel methods, devices, and apparatus relating to Ophthalmic Lenses with passive event coloration mechanisms are therefore important.

SUMMARY

Accordingly, the present invention includes innovations relating to a method of manufacturing an Ophthalmic Lens with an event coloration mechanism. The method may comprise the steps of forming a lens, wherein the lens may comprise a soft biocompatible material; and encapsulating an event coloration mechanism within the lens, wherein the event coloration mechanism may be capable of triggering a visual indication in the Ophthalmic Lens based on an occurrence of a predefined event, such as, for example, a change in pH in the ocular environment.

The method may further comprise the steps of adding a Reactive Monomer Mixture to one or both a front curve mold and a back curve mold part; placing the back curve mold proximate to the front curve mold; curing the Reactive Monomer Mixture to form the Ophthalmic Device; demolding the front curve mold part and the back curve part; removing Ophthalmic Lens from the demolded front curve mold and back curve. In some embodiments, the method may also comprise hydrating the Ophthalmic Lens.

In some embodiments, the event coloration mechanism may further comprise a reservoir containing a substance, wherein the substance may be capable of coloration by reacting to a predefined constituent or a predefined condition of the tear fluid of the eye; and an encapsulating layer, wherein the encapsulating layer may be capable of encapsulating the reservoir. For example, the event coloration mechanism may comprise liquid crystal, wherein the liquid crystal may be capable of altering color based on a temperature change in the ocular environment. Alternatively, the encapsulating layer may be selectively permeable to the predefined constituent of the tear fluid, wherein the predefined constituent may be indicative of the predefined event.

In some embodiments, the encapsulating may occur after the curing, and the encapsulating may further comprise the method steps of injecting the event mechanism into the lens at a predefined depth. Alternatively, the encapsulating may occur before the curing, and the encapsulating may further comprise the method steps of injecting the event coloration mechanism into a location that will be between the front curve mold part and the back curve mold part. In some such embodiments, the curing of the Reactive Monomer Mixture may be capable of securing the event coloration mechanism within the lens. The curing may be capable of curing the encapsulating layer of the event coloration mechanism.

In some embodiments, the event coloration mechanism may further comprise a Rigid Insert. For example, the Rigid Insert may comprise an annular shape capable of framing an Optic Zone of the eye. Where the encapsulating occurs prior to curing, the encapsulating may further comprise the method steps of placing the event coloration mechanism in a location that will be between the front curve mold part and the back curve part. Alternatively, the encapsulating may occur after the curing, and the encapsulating may further comprise the method steps of inserting the event coloration mechanism into the lens. Where the encapsulating occurs after the curing, the encapsulating may further comprise the method steps of inserting the event coloration mechanism into the lens.

In still other embodiments, the encapsulating may further comprise the method steps of anchoring a reactive molecule within the lens. The reactive molecule may comprise a binding portion capable of binding with the predefined constituent; an acceptor coloration portion located on a first end of the binding portion; and a donor coloration portion located on a second end of the binding portion. The binding may be capable of altering a configuration of the reactive molecule, wherein a change in configuration may be capable of providing the visual indication.

In some embodiments, the encapsulating may occur prior to curing the Reactive Mixture and may further comprise mixing the event coloration mechanism with the Reactive Monomer Mixture. In such embodiments, the method may further comprise the method steps of curing the event coloration mechanism. The curing of the event coloration mechanism may comprise a separate curing process than the curing of the Reactive Monomer Mixture. Alternatively, at least a portion of the curing of the event coloration mechanism and at least a portion of the curing of the Reactive Monomer Mixture may occur simultaneously.

DETAILED DESCRIPTION OF THE INVENTION

The present invention describes an Ophthalmic Lens device with passive event coloration mechanisms. In general, according to some embodiments of the present invention, passive event coloration mechanisms may be incorporated with an Ophthalmic Lens, including those with a Rigid Insert or Media Insert. Passive event coloration mechanisms may be "activated" without requiring a power source, but instead may interface or interact with an ocular environment. This proximity with the ocular environment may allow for a wide range of events.

In some embodiments, for example, the event may be a specific or threshold concentration of a biomarker within the tear fluid. Monitoring the concentration of certain biomarkers within tear fluid may allow a patient or doctor to develop a more effective therapy schedule, such as with light therapy and melatonin levels. Alternatively, the coloration may be able to alert the patient of ineffective or dangerous levels of the biomarker, which may be high levels or low levels, depending on the biomarker. For example, high levels of glucose in a diabetic patient may require an emergency response.

An alternative example of an event may be medication levels in the tear fluid. Some medications are most effective within a specific concentration range, and some may even be dangerous at concentrations above that range. Such medications may include, for example, those that treat mental disorders, thyroid diseases, or degenerative brain diseases, such as, Alzheimer's disease.

For example, valproic acid is a common medication that may treat epilepsy or bipolar, in lower doses. Frequent blood tests may be required to monitor the concentration of the medication to ensure the concentration is within the therapeutic range and not into the toxic range, which may cause, for example, renal failure or increase in symptoms of the mental disorder. A constant monitoring system may allow a patient to maintain safe and effective levels.

Other events may include the presence or concentration of specific pathogens, for example, those that may cause ocular infections or may be indicative of non-ocular infections or diseases, such as keratitis, conjunctivitis, corneal ulcers, and cellulitis. Such pathogens may include, for example, *Acanthamoeba keratitis, Pseudomona aeruginosa, Neisseria gonorrhoeae*, and *Staphylococcus* and *Streptococcus* strains, such as *S. aureus*.

In the following sections, detailed descriptions of embodiments of the invention will be given. The description of both preferred and alternative embodiments are exemplary embodiments only, and it is understood that to those skilled in the art that variations, modifications, and alterations may be apparent. It is therefore to be understood that said exemplary embodiments do not limit the scope of the underlying invention.

Glossary

In this description and claims directed to the presented invention, various terms may be used for which the following definitions will apply:

Back Curve Piece or Back Insert Piece: as used herein refers to a solid element of a multi-piece Rigid Insert which when assembled into the said insert will occupy a location on the side of the lens that is on the back. In an Ophthalmic Device, said piece may be located on the side of the insert that would be closer to the user's eye surface. In some embodiments, the back curve piece may contain and include a region in the center of an Ophthalmic Device through which light may proceed into the user's eye, which may be called an Optic Zone. In other embodiments, the piece may take an annular shape where it does not contain or include some or all of the regions in an optic zone. In some embodiments of an ophthalmic insert, there may be multiple back curve pieces and one of them may include the optic zone, while others may be annular or portions of an annulus.

Component: as used herein refers to a device capable of drawing electrical current from an Energy Source to perform one or more of a change of logical state or physical state.

Encapsulate: as used herein refers to creating a barrier to separate an entity, such as, for example, a Media Insert, from an environment adjacent to the entity.

Encapsulant: as used herein refers to a layer formed surrounding an entity, such as, for example, a Media Insert, that creates a barrier to separate the entity from an environment adjacent to the entity. For example, Encapsulants may be comprised of silicone hydrogels, such as Etafilcon, Galyfilcon, Narafilcon, and Senofilcon, or other hydrogel contact lens material. In some embodiments, an Encapsulant may be semipermeable to contain specified substances within the entity and preventing specified substances, such as, for example, water, from entering the entity.

Energized: as used herein refers to the state of being able to supply electrical current to or to have electrical energy stored within.

Energy: as used herein refers to the capacity of a physical system to do work. Many uses within this invention may relate to the said capacity being able to perform electrical actions in doing work.

Energy Source: as used herein refers to device capable of supplying Energy or placing a biomedical device in an Energized state.

Event: as used herein refers to a defined set of parameters, such as, for example, a biomarker level, energization level, pH level, or a visual recognition of a particular object. An event may be specific to a wearer, such as a level of medication, or may be generally applicable to all wearers, such as temperature.

Front Curve Piece or Front Insert Piece: as used herein refers to a solid element of a multi-piece Rigid Insert which when assembled into the said insert will occupy a location on the side of the lens that is on the front. In an Ophthalmic Device, a Front Curve Piece would be located on the side of the insert that would be further from the user's eye surface. In some embodiments, the piece may contain and include a region in the center of an Ophthalmic Device through which light may proceed into the user's eye, which may be called an Optic Zone. In other embodiments, the piece may take an annular shape where it does not contain or include some or all of the regions in an optic zone. In some embodiments of an ophthalmic insert, there may be multiple front curve pieces and one of them may include the optic zone, while others may be annular or portions of an annulus.

Lens-forming mixture or Reactive Mixture or Reactive Monomer Mixture (RMM): as used herein refers to a monomer or prepolymer material that can be cured and cross-linked or cross-linked to form an Ophthalmic Lens. Various embodiments can include lens-forming mixtures with one or more additives such as UV blockers, tints, photoinitiators or catalysts, and other additives one might desire in an Ophthalmic Lenses such as, contact or intraocular lenses.

Lens-forming Surface: as used herein refers to a surface that is used to mold a lens. In some embodiments, any such surface can have an optical quality surface finish, which indicates that it is sufficiently smooth and formed so that a lens surface fashioned by the polymerization of a lens forming material in contact with the molding surface is optically acceptable. Further, in some embodiments, the lens-forming surface can have a geometry that is necessary to impart to the lens surface the desired optical characteristics, including without limitation, spherical, aspherical and cylinder power, wave front aberration correction, corneal topography correction and the like as well as any combinations thereof.

Liquid Crystal: as used herein refers to a state of matter having properties between a conventional liquid and a solid crystal. A Liquid Crystal cannot be characterized as a solid but its molecules exhibit some degree of alignment. As used herein, a Liquid Crystal is not limited to a particular phase or structure, but a Liquid Crystal may have a specific resting orientation. The orientation and phases of a Liquid Crystal may be manipulated by external forces such as, for example, temperature, magnetism, or electricity, depending on the class of Liquid Crystal.

Lithium Ion Cell: as used herein refers to an electrochemical cell where Lithium ions move through the cell to generate electrical energy. This electrochemical cell, typically called a battery, may be reenergized or recharged in its typical forms.

Media Insert: as used herein refers to an encapsulated insert that will be included in an energized Ophthalmic Device. The energization elements and circuitry may be embedded in the Media Insert. The Media Insert defines the primary purpose of the energized Ophthalmic Device. For example, in embodiments where the energized Ophthalmic Device allows the user to adjust the optic power, the Media Insert may include energization elements that control a liquid meniscus portion in the Optical Zone. Alternatively, a Media Insert may be annular so that the Optical Zone is void of material. In such embodiments, the energized function of the Lens may not be optic quality but may be, for example, monitoring glucose or administering medicine.

Mold: as used herein refers to a rigid or semi-rigid object that may be used to form lenses from uncured formulations. Some preferred molds include two mold parts forming a front curve Mold part and a back curve Mold part.

Ophthalmic Lens or Ophthalmic Device or Lens: as used herein refers to any device that resides in or on the eye, in contrast to a spectacle lens. The device may provide optical correction, may be cosmetic, or provide some functionality unrelated to optic quality. For example, the term Lens may refer to a contact Lens, intraocular Lens, overlay Lens, ocular insert, optical insert, or other similar device through which vision is corrected or modified, or through which eye physiology is cosmetically enhanced (e.g. iris color) without impeding vision. Alternatively, Lens may refer to a device that may be placed on the eye with a function other than vision correction, such as, for example, monitoring of a constituent of tear fluid or means of administering an active agent. In some embodiments, the preferred Lenses of the invention may be soft contact Lenses that are made from silicone elastomers or hydrogels, which may include, for example, silicone hydrogels and fluorohydrogels.

Optic Zone: as used herein refers to an area of an Ophthalmic Lens through which a wearer of the Ophthalmic Lens sees.

Power: as used herein refers to work done or energy transferred per unit of time.

Reenergize or Recharge: as used herein refers to a restoration to a state with higher capacity to do work. Many uses within this invention may relate to restoring a device to the capability to flow electrical current at a certain rate for a specified, reestablished time period.

Released from a mold: as used herein refers to a lens is either completely separated from the mold, or is only loosely attached so that it can be removed with mild agitation or pushed off with a swab.

Rigid Insert: as used herein refers to an insert that maintains a predefined topography and includes a greater modulus than a hydrogel in contact with all or part of the Rigid Insert. When included in a Contact Lens, the Rigid Insert may contribute to the functionality of the Lens. For example, varying topography of or densities within the Rigid Insert may define zones, which may correct vision in users with astigmatism.

Three-dimensional Surface or Three-dimensional Substrate: as used herein refers to any surface or substrate that has been three-dimensionally formed where the topography is designed for a specific purpose, in contrast to a planar surface.

Ophthalmic Lens with an Event Coloration Mechanism

Non-Energizable Event Coloration Mechanisms

Figure 1:
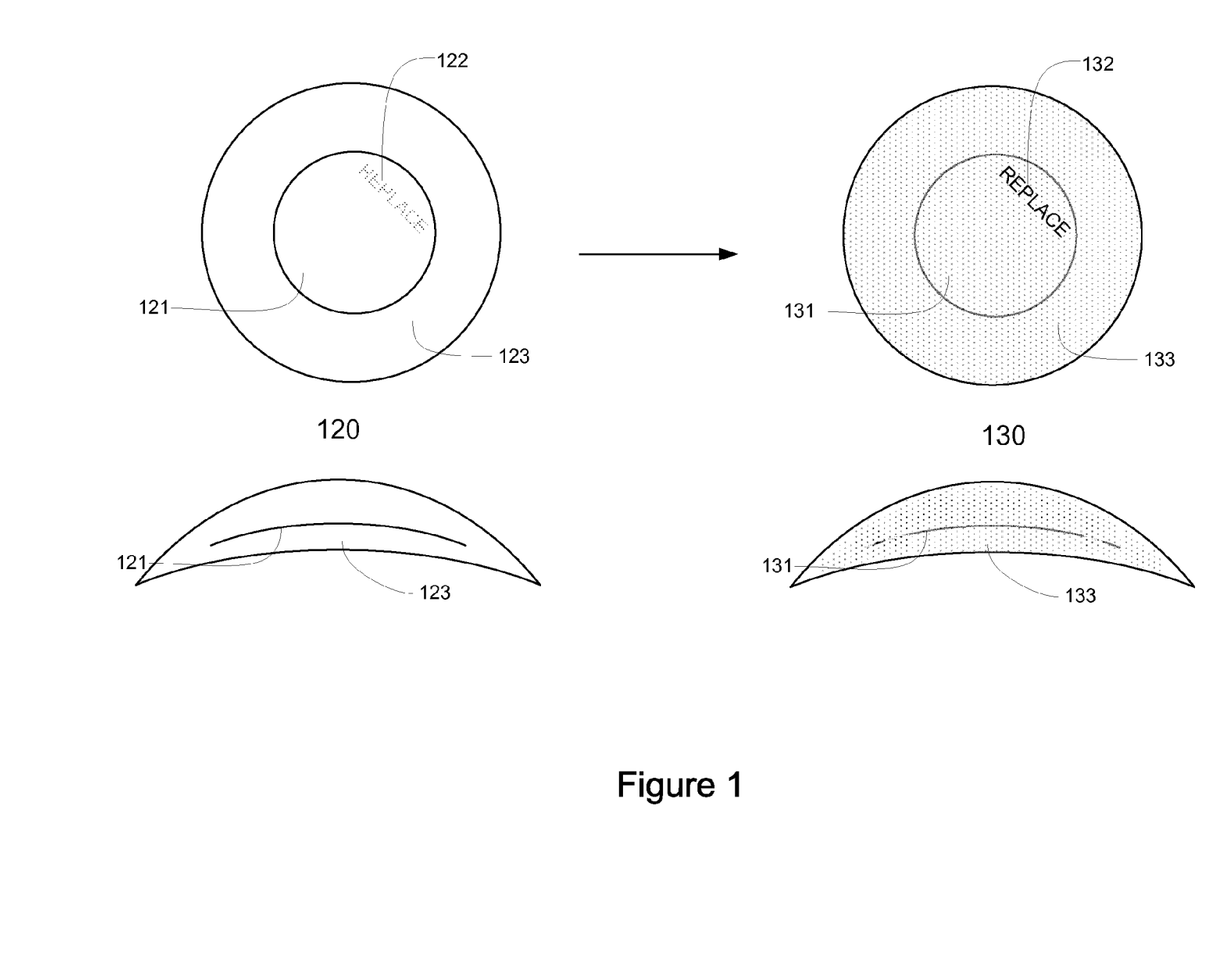
FIG. 1 illustrates an exemplary embodiment of an Ophthalmic Lens with a passive event coloration mechanism.

Proceeding to FIG. 1, an example of a Rigid Insert 121 with a non-energizable event coloration mechanism 122 is illustrated. In some embodiments, an event coloration mechanism 122 may comprise a reactive mixture, which, for example, may be added to, printed on, or embedded in a Rigid Insert 121, such as through thermoforming techniques. Alternatively, not shown, the event coloration mechanism 122 may not require a Rigid Insert 121 but instead may be located on or within the hydrogel portion 123, for example, through use of printing or injection techniques.

The event coloration mechanism 122 may comprise a portion of the Rigid Insert 121 that is reactive to some component of the transient tear fluid or some component within the Ophthalmic Lens 120. For example, the event may be a specific accumulation of some precipitant, such as, lipids or proteins, on either or both the Rigid Insert 131 and the hydrogel portion 133, depending on the composition of the Ophthalmic Lens 130. The accumulation level may "activate" the event coloration mechanism 132 without requiring a power source. The activation may be gradual wherein the color becomes more visible as the accumulation level increases, which may indicate when the Ophthalmic Lens 130 needs to be cleaned or replaced.

Alternatively, the color may only be apparent at a specific level. In some embodiments, the activation may be reversible, such as, for example, where the wearer effectively removes the precipitant from the hydrogel portion 133 or the Rigid Insert 131. The event coloration mechanism 132 may be located outside the Optic Zone, which may allow for an annular embodiment of the Rigid Insert, not shown. In other embodiments, particularly where the event may prompt a wearer to take immediate action, the event coloration mechanism 132 may be located within the Optic Zone, allowing the wearer to see the activation of the event coloration mechanism 132.

In some other embodiments, the event coloration mechanism, not shown, may comprise a reservoir containing a colored substance, such as, for example, a dye. Prior to the occurrence of the event, the reservoir may not be visible. The reservoir may be encapsulated with a degradable material, which may be irreversibly degraded by some constituent of the tear fluid, including, for example, proteins or lipids. Once degraded, the colored substance may be released into the Ophthalmic Lens 130 or into a second reservoir. Such an embodiment may indicate when a disposable Ophthalmic Lens 130 should be disposed, for example, based on a manufacturer's recommended parameters.

Figure 2:
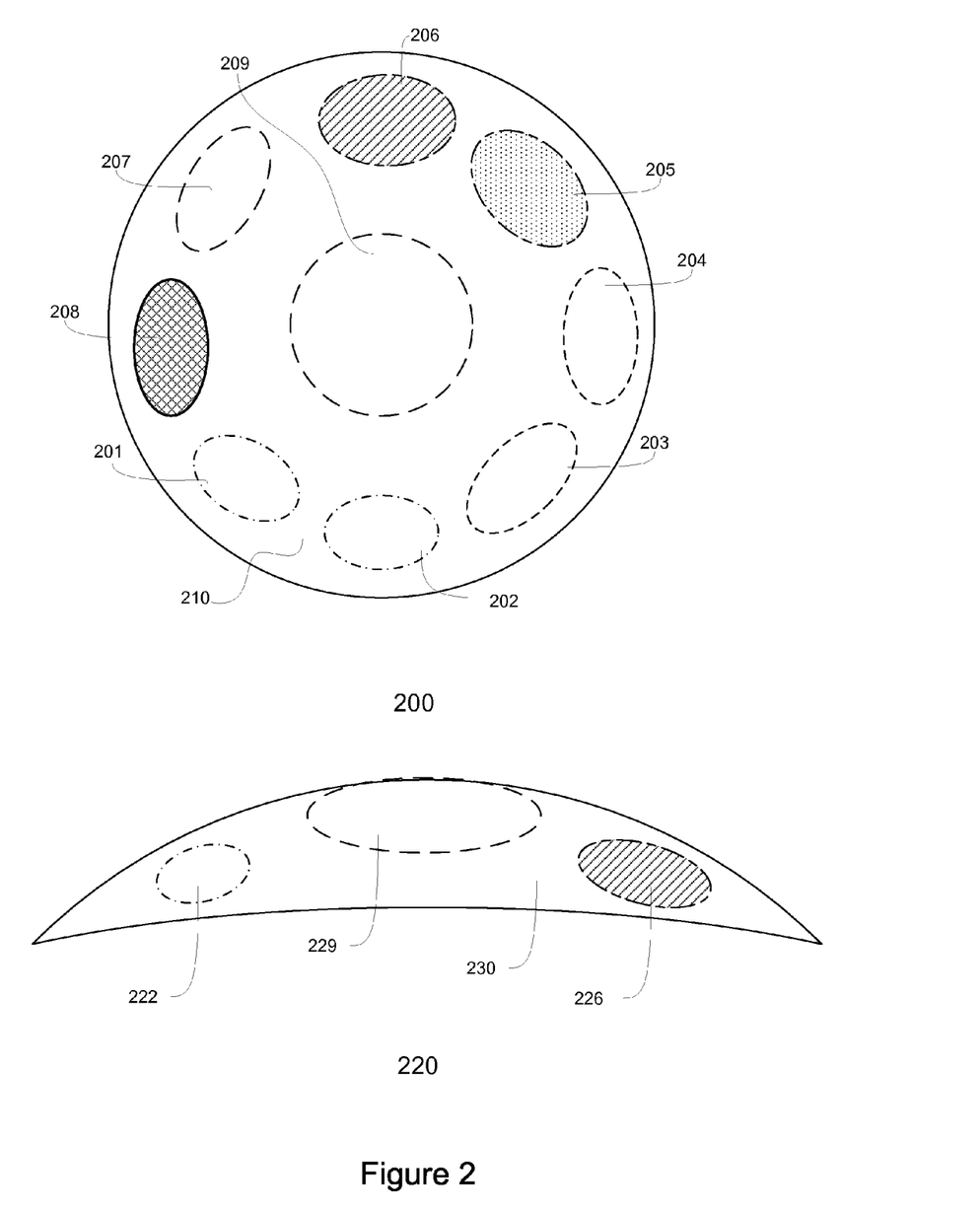
FIG. 2 illustrates an alternate embodiment of passive event coloration mechanisms included in an Ophthalmic Lens.

Proceeding to FIG. 2, an exemplary embodiment of an Ophthalmic Lens 200 with multiple event coloration mechanisms 201-208 is illustrated. In some embodiments, the event coloration mechanisms 201-208 may be located within the soft, hydrogel portion 210 of the Ophthalmic Lens 200 and outside the Optic Zone 209. Such embodiments may not require a Rigid Insert or Media Insert for functioning of the event coloration mechanisms 201-208, though inserts may still be incorporated in the Ophthalmic Lens 200 allowing for additional functionalities.

In some embodiments, each event coloration mechanism 201-208 may be separately encapsulated within the soft, hydrogel portion 210 of the Ophthalmic Lens. The contents of the event coloration mechanisms 201-208 may include a compound reactive to some condition, such as temperature, or component of tear fluid, such as a biomarker.

In some embodiments, each event coloration mechanism 201-208 may "activate" based on different events. For example, one event coloration mechanism 208 may comprise liquid crystal that may react to changes in temperatures of the ocular environment, wherein the event is a fever. Other event coloration mechanisms 202-206 within the same Ophthalmic Lens 200 may react to specific pathogens, for example, those that may cause ocular infections or may be indicative of non-ocular infections or diseases, such as keratitis, conjunctivitis, corneal ulcers, and cellulitis. Such pathogens may include, for example, *Acanthamoeba keratitis, Pseudomona aeruginosa, Neisseria gonorrhoeae*, and *Staphylococcus* and *Streptococcus* strains, such as *S. aureus*.

The event coloration mechanisms 201-207 may be encapsulated with a compound that may be selectively permeable to a component of tear fluid. In some embodiments, the event coloration mechanism 202-206 may function by agglutination, such as through a coagulase test, wherein a higher concentration of the pathogen may adhere to a compound within the event coloration mechanism 202-206 and may cause clumping or the formation of precipitate. The precipitate may provide coloration or may react with another compound in the event coloration mechanism 202-206 through a separate reaction. Alternatively, the event coloration mechanism 202-206 may comprise a reagent that colors upon reaction, such as with some oxidase tests.

In still other embodiments, an event coloration mechanism 202-206 may function similarly to a litmus test, wherein the event coloration mechanism activates based on the pH or pOH within the ocular environment. For example, to monitor the concentration of valproic acid, the event coloration mechanism may contain specific proteins that would be able to bind to the valproic acid up to a specific concentration. The non-binding valproic acid may be indicative of the effective quantities within the tear fluid. The pH or pOH within the event coloration mechanism may increase with the increased concentration of the acid.

Other exemplary coloration mechanisms 201 may be reactive to ultraviolet rays, wherein the event may be overexposure of the eye to UV light, as with snow blindness. Another coloration mechanism 207 may react to protein accumulation, such as described with FIG. 1.

Some event coloration mechanisms 208 may be reversible, such as when the wearer has effectively responded to the event. For example, after a wearer has rinsed the Ophthalmic Lens, the level of pathogens or protein may be sufficiently reduced to allow for safe use of the Ophthalmic Lens. Alternatively, the coloration may be reversible on the eye, such as where the event is a fever and the wearer's temperature has been effectively lowered.

As shown in cross section, the event coloration mechanisms 222, 226 may be located in the periphery of the Ophthalmic Lens 220 without altering the optical surface of the hydrogel portion 230. In some embodiments, not shown, the event coloration mechanisms may be at least partially within the Optic Zone 229, alerting the wearer of the event. The locations of the event coloration mechanisms 222, 226 may be varied within a single Ophthalmic Lens 220, with some in the periphery and some within the Optic Zone 229.

The event coloration mechanisms 201-208 may be independently activated. For example, the wearer may have a fever, triggering a change in coloration in liquid crystal contained in an event coloration mechanism 208. Two other event coloration mechanisms 205, 206 may indicate high levels of *S. aureus* and *A. keratitis*, which may provide guidance on what is causing the fever, particularly where other symptoms corroborate the diagnosis. Where the event coloration mechanisms 201-208 serve as diagnostic tools, the coloration may not be reversible, allowing the wearer to remove the Ophthalmic Lens 200 without losing the event indication.

In some embodiments, the event coloration mechanism 208 may be coated in a substance with low permeability, such as, for example, parylene. This embodiment may be particularly significant where the event coloration mechanism 208 contains compounds that may be dangerous if in contact with the eye or where the event does not require interaction with the tear fluid. For example, where the event is a temperature change, a liquid crystal droplet may be parylene coated, which may be further strengthened into a hermetic seal by alternating the parylene with a fortifying compound, such as, silicon dioxide, gold, or aluminum.

For exemplary purposes, the Ophthalmic Lens 200 is shown to include eight event coloration mechanisms. However, it may be obvious to those skilled in the art that other quantities of event coloration mechanisms may be practical.

Figure 3:
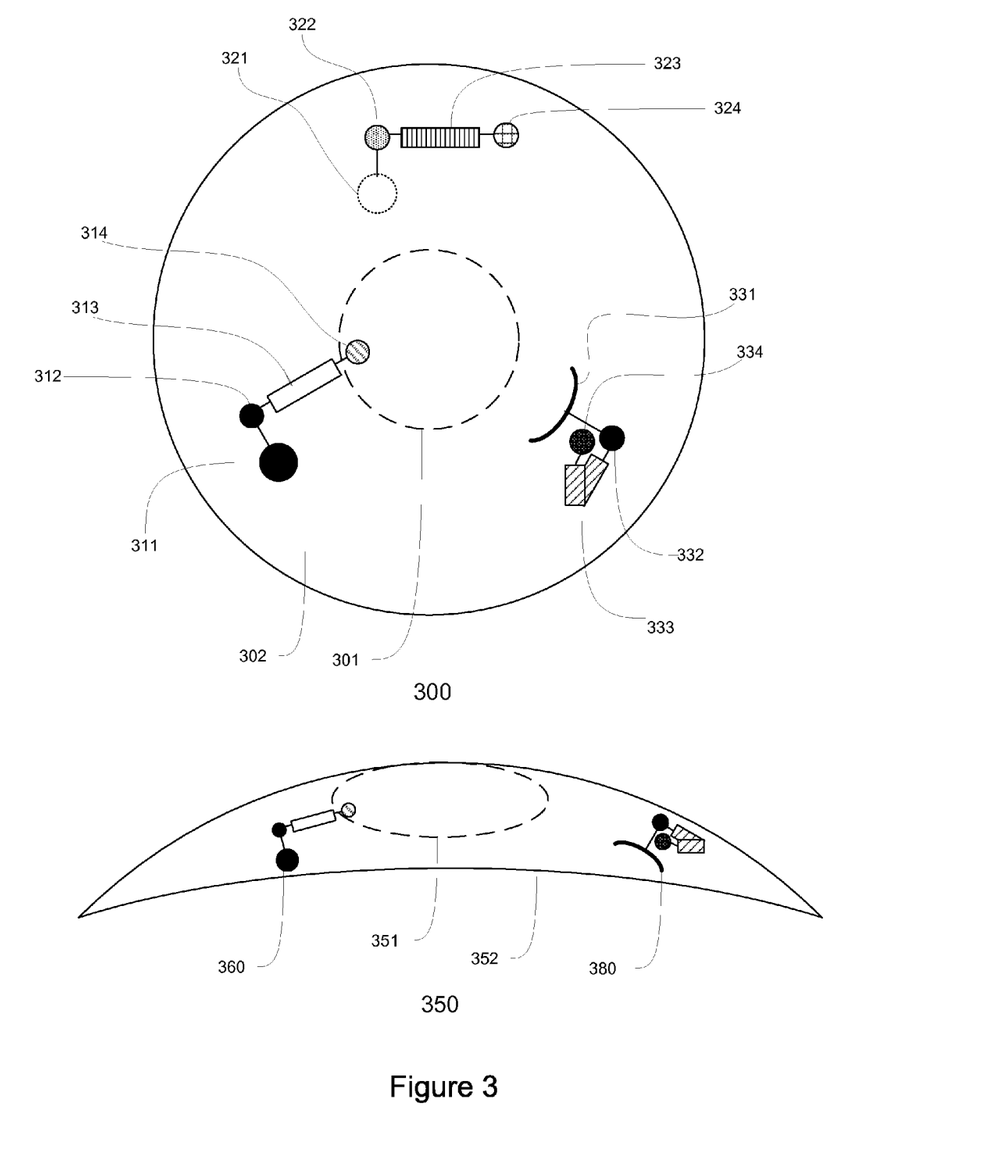
FIG. 3 illustrates an alternate embodiment of passive event coloration mechanisms included in an Ophthalmic Lens.

Proceeding to FIG. 3, an alternative embodiment of an Ophthalmic Lens 300 with event coloration mechanisms 311-314, 321-324, 331-334 is illustrated. In some such embodiments, the event mechanisms 311-314, 321-324, 331-334 may include a reactive molecule 312-314, 322-324, 332-334 anchored within the Ophthalmic Lens.

The reactive molecule 312-314, 332-334 may comprise a central binding portion 313, 333 flanked by a quencher 312, 331 and a coloration portion 314, 334, such as, for example, a chromophore or fluorophore. Depending on the molecular structure, when a specified compound binds to the binding portion 313, 333, the coloration portion 314, 334 may shift closer to the quencher 312, reducing coloration, or may shift away from the quencher 332, which would increase coloration. In other embodiments, the reactive molecule 322-324 may comprise a binding portion 323 flanked by Förster resonance energy transfer (FRET) pairs 322, 324. FRET pairs 322, 324 may function similarly to a quencher 312, 332 and chromophore 314, 334, though FRET pairs 322, 324 may both exhibit coloration and, when in close proximity to each other, their spectral overlap may cause a change in coloration.

The reactive molecule 312-314, 322-324, 332-334 may be selected to target specific compounds within the tear fluid. In some embodiments, the specific compound may directly indicate the event. For example, where a level of glucose in the tear fluid is the event, the reactive molecule 312-314, 322-324, 332-334 may directly bind with the glucose. Where the event is the presence or concentration of a pathogen, for example, a particular aspect of that pathogen may bind with the reactive molecule 312-314, 322-324, 332-334. This may include a unique lipid or protein component of that pathogen. Alternatively, the specific compound may be an indirect indicator of the event. The specific compound may be a byproduct of the pathogen, such as a particular antibody that responds to that pathogen.

In some embodiments, the reactive molecule 312-314 may be anchored within the Ophthalmic Lens by a secondary compound 311, such as, for example, a protein, peptide, or aptamer. Alternatively, the hydrogel 302 may provide a sufficient anchor 321 to secure the reactive molecule 322-324 within the Ophthalmic Lens 300. The reactive molecule 322-324 may be in contact with the Reactive Monomer Mix prior to polymerization, which may allow the reactive molecule 322-324 to chemically bind with the hydrogel 321. The reactive molecule may be injected into the hydrogel after polymerization but before hydration, which may allow precise placement of the reactive molecule.

In some embodiments, tinting the anchoring mechanism may provide broader cosmetic choices. The Ophthalmic Lens may further comprise a limbic ring or an iris pattern, which may provide a static and natural background or foreground to the event coloration mechanisms. The design pattern may be included on or within the hydrogel or may be included in a Rigid Insert through a variety of processes, such as, for example, printing on a surface of the Rigid Insert. In some such embodiments, the periphery event coloration mechanisms may be arranged to appear less artificial, for example through a sunburst pattern that may more naturally integrate into the wearer's iris pattern or an iris pattern included in the Ophthalmic Lens than random dotting throughout the Ophthalmic Lens.

In other embodiments, the reactive molecule 332-334 may be anchored to a Rigid Insert 331. The Rigid Insert, not shown, may be annular and may anchor multiple reactive molecules outside of the Optic Zone 301. Alternatively, the Rigid Insert 331 may be a small periphery insert, which may anchor a single reactive molecule 332-334 or many of the same reactive molecules, which may allow for a more vibrant coloration.

As illustrated in cross section, the placement of the reactive molecules 360, 380 within the Ophthalmic Lens 350 may be varied within the hydrogel 352. For example, some reactive molecules 380 may be entirely in the periphery with no overlap with the Optic Zone 351. Other reactive molecules 360 may at least partially extend into the Optic Zone 351. In some such embodiments, the reactive molecules 360 may extend into the Optic Zone 351 in some configurations of that reactive molecule 360, such as when the event has occurred, which may alert the wearer of the event.

Figure 4:
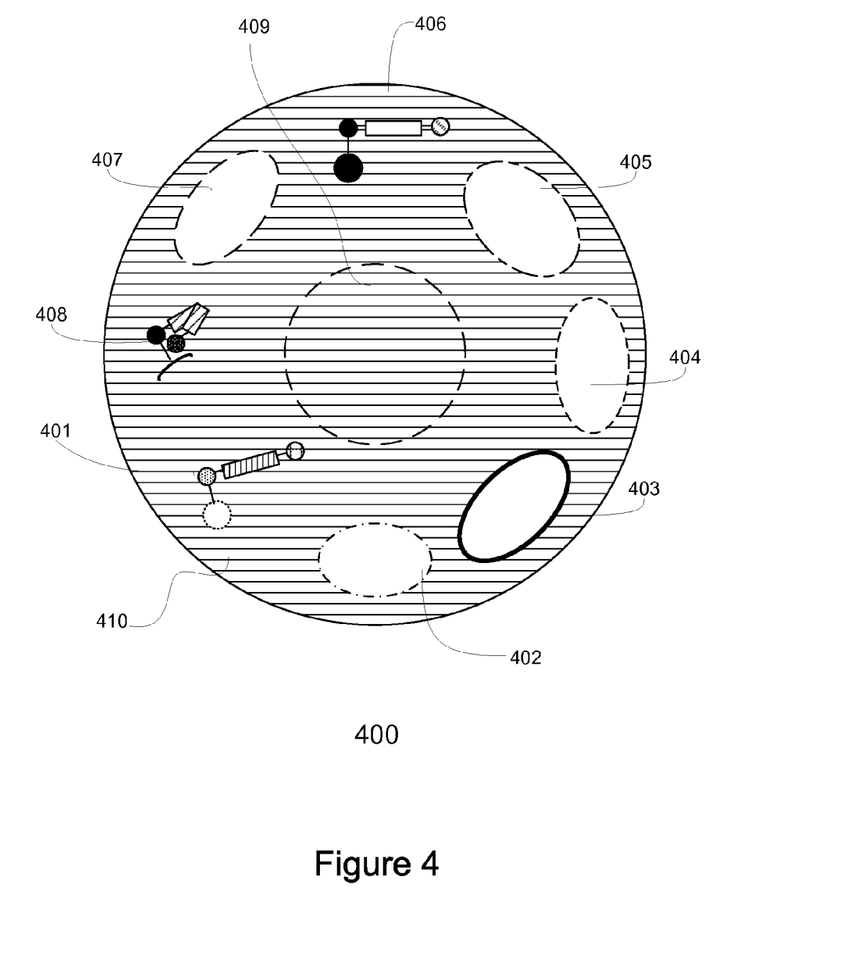
FIG. 4 illustrates an alternate embodiment of an Ophthalmic Lens with a passive event coloration mechanism.

Proceeding to FIG. 4, an exemplary embodiment of an Ophthalmic Lens 400 with a variety of event coloration mechanisms 401-408, 410 is illustrated. Some Ophthalmic Lenses 400 may comprise a combination of event coloration mechanism embodiments. For example, the event coloration mechanisms may include FRET pairs 401, parylene-coated liquid crystal 403, Rigid Insert anchored quencher 408, secondary compound anchored quencher 406, selectively permeable reservoirs 402, 404, 405, 407.

An event coloration mechanism may also be integrated with the hydrogel portion 410. For example, a reactive molecule may be mixed with the Reactive Monomer Mixture prior to polymerization. In some such embodiments, the event coloration mechanism may be dispersed throughout the hydrogel 410, including over the Optic Zone 409.

In some embodiments, the varied event coloration mechanisms 401-408 may indicate a mix of events, which may be tailored according to a patient's needs. For example, the event coloration mechanisms may indicate a series of event related to a single disorder. In some such embodiments, one event coloration mechanism may change color with an increase in glucose levels, and another event coloration mechanism may lose color when a diabetic medication is in low concentration. Such an embodiment may act as a reminder to the patient to take their medication or may allow the patient to eat accordingly. Another example may include monitoring serotonin levels in a first event coloration mechanism and depression medications in other event coloration mechanisms. This may be particularly significant where a patient takes a combination of medications.

Figure 5:
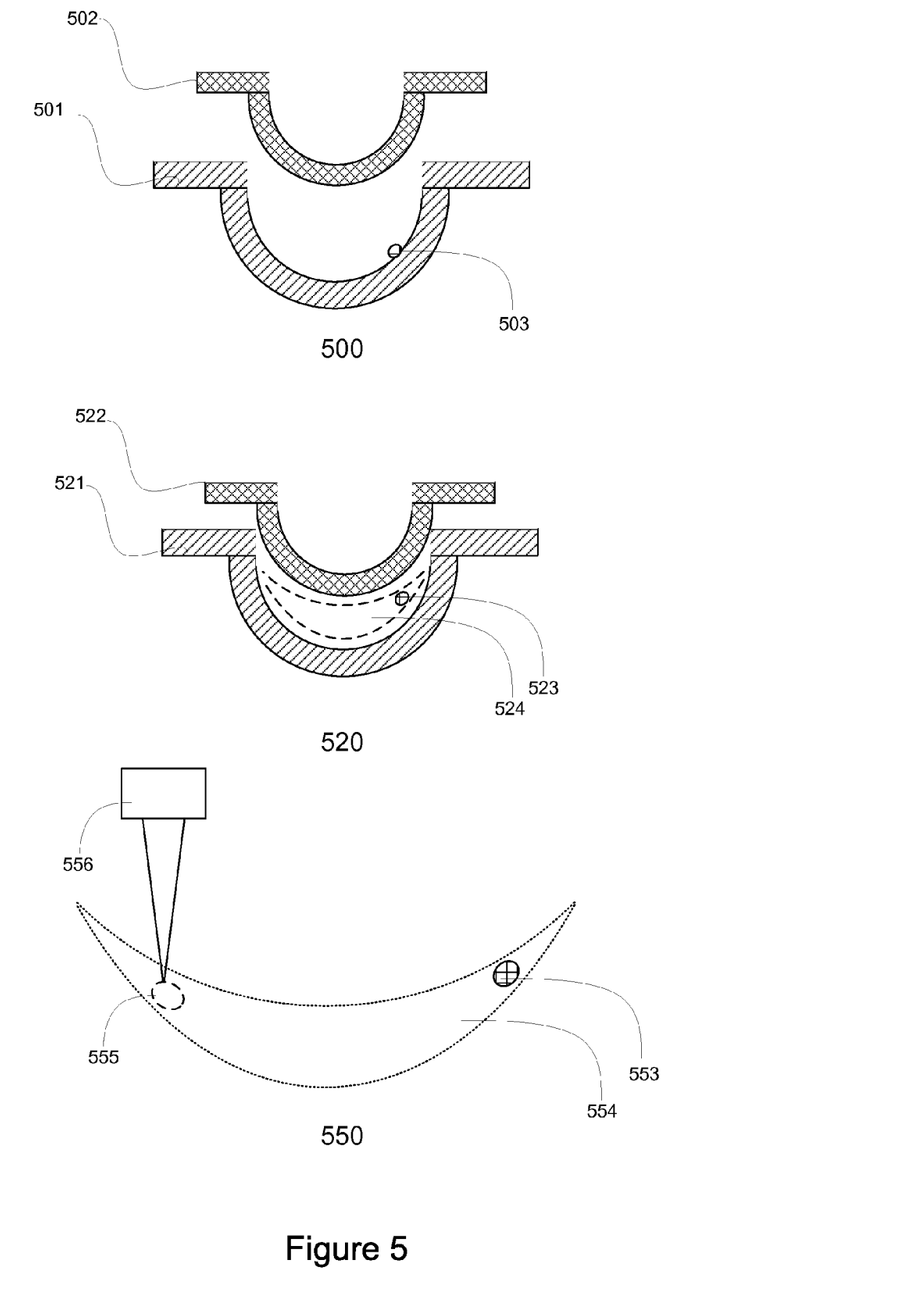
FIG. 5 illustrates an exemplary flowchart of method steps for manufacturing an Ophthalmic Lens with passive event coloration mechanisms.

Proceeding to FIG. 5, an exemplary method step flowchart 500, 520, 550 for manufacturing an Ophthalmic Lens 550 with passive coloration mechanisms 555, 553 is illustrated. In some embodiments, the Ophthalmic Lens 550 may be formed through injection molding techniques, for example, through polymerization of Reactive Monomer Mixture 524 between a front curve mold piece 501 and back curve mold piece 502. It may be apparent to one ordinarily skilled in the art that other techniques, such as free form lithography, may be practical.

An event coloration mechanism 503 may be placed in the molding apparatus 501, 502 prior to the addition of the Reactive Monomer Mixture 524. In some such embodiments, the Reactive Monomer Mixture 524 may encapsulate the event coloration mechanism 523 when the front curve mold piece 521 is placed in proximity to the back curve mold piece 522, and polymerization of the RMM may secure the event coloration mechanism 523 within the Ophthalmic Lens 550. In embodiments with inserts, such as a Rigid Insert or Media Insert, the inclusion of the event coloration mechanisms 555, 553 may occur prior to, after, or in conjunction with the inserts.

As illustrated in FIG. 4, an event coloration mechanism may be mixed with the RMM prior to polymerization, allowing the dispersion of the event coloration mechanism throughout at least a portion of the hydrogel. An event coloration mechanism 555 may be included within the Ophthalmic Lens 550 after polymerization of the RMM, such as, for example, through an injection mechanism 556. Such an injection may occur prior to hydration in some embodiments, which may allow for precise placement of the event coloration mechanism within the still-hard hydrogel 554. For illustrative purposes, the event coloration mechanisms 555, 553 are shown as droplets (as described with FIG. 2), but other embodiments, such as those previously discussed, may be included within an Ophthalmic Lens 550 using similar techniques.

Figure 6:
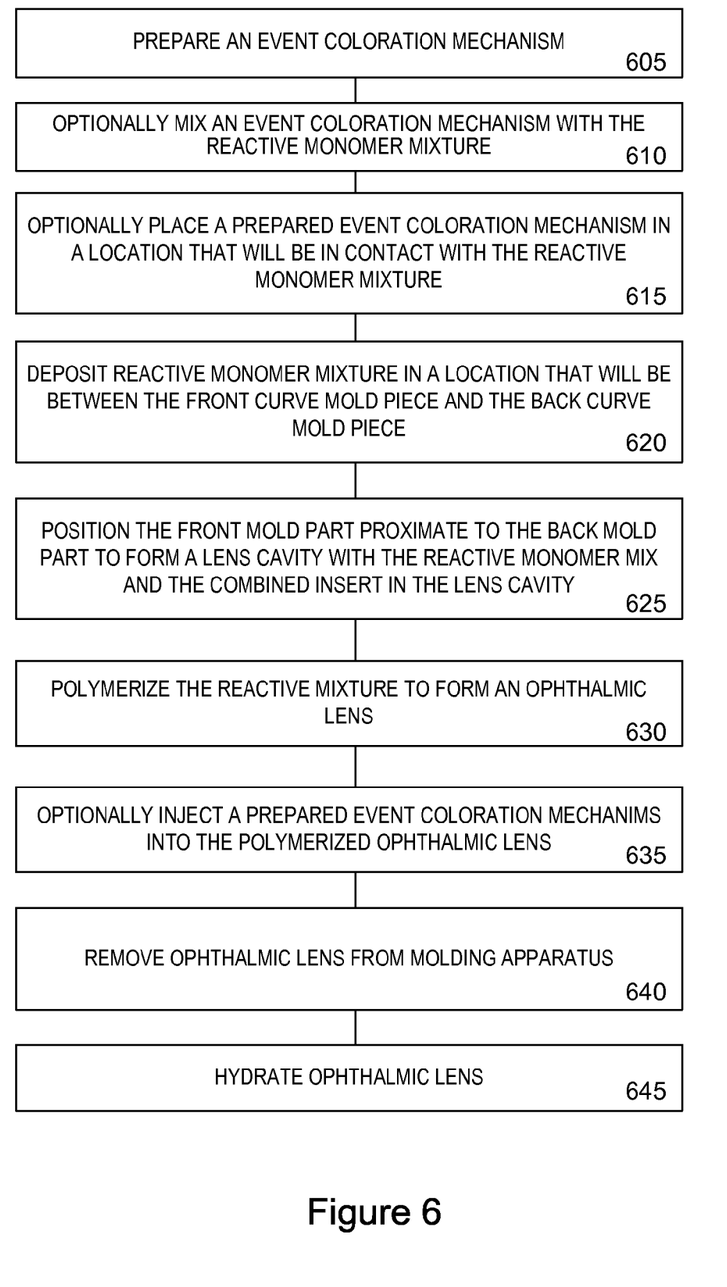
FIG. 6 illustrates exemplary method steps for manufacturing an Ophthalmic Lens with passive event coloration mechanisms.

Proceeding to FIG. 6, exemplary method steps for forming an Ophthalmic Lens with passive event coloration mechanisms are illustrated. At 605, an event coloration mechanism may be prepared. The preparation may include formulating a molecular structure that may allow the molecule may react with the specified compound in the tear fluid, wherein the reaction may prompt a coloration or color change. In some embodiments, the preparation may include, for example, adding anchoring compounds or encapsulating a reagent or liquid crystal droplet.

In some embodiments, at 610, an event coloration mechanism may optionally be mixed with the Reactive Monomer Mixture, which may allow for the dispersion of the event coloration mechanism within at least a portion of the Ophthalmic Lens. At 615, a prepared event coloration mechanism may optionally be placed in a location that will be in contact with the RMM, such as, for example, on the front curve mold piece or between the front and back curve mold pieces.

At 620, RMM may be added in a location that will be between the front curve and back curve mold pieces, such as, for example, by injecting the RMM onto the front curve mold piece. At 625, the front curve mold piece may be placed in proximity to the back curve mold piece to form a lens cavity, which may allow the RMM to encapsulate the placed event coloration mechanism. At 630, the RMM may be polymerized to form the Ophthalmic Lens. In some embodiments, at 630, the event coloration mechanisms may also be polymerized, such as, for example, where a reactive molecule may be anchored to hydrogel or where the event coloration mechanism may be mixed in with the RMM.

At 635, an event coloration mechanism may optionally be inserted or injected into the polymerized Ophthalmic Lens. At 640, the Ophthalmic Lens may be removed from the molding apparatus, and at 645, the Ophthalmic Lens may be hydrated. In some embodiments, the insertion at 635 may occur prior to hydration and removal from the apparatus. Alternatively, the insertion at 635 may occur after the Ophthalmic Lens has been removed from the apparatus, but prior to hydration.

Materials for Insert Based Ophthalmic Lenses

In some embodiments, a lens type can be a lens that includes a silicone-containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

In some embodiments, the Ophthalmic Lens skirt, which sometimes may be called an insert encapsulating layer, that surrounds the insert may be comprised of standard hydrogel lens formulations. Exemplary materials with characteristics that may provide an acceptable match to numerous insert materials may include the Narafilcon family; including Narafilcon A and Narafilcon B. Alternatively, the Etafilcon family; including Etafilcon A may represent good exemplary material choices. A more technically inclusive discussion follows on the nature of materials consistent with the art herein; but it may be clear that any material that may form an acceptable enclosure or partial enclosure of the sealed and encapsulated inserts are consistent and included.

Suitable silicone containing components include compounds of Formula I where:

$R^1$ is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof;

where b=0 to 500, where it is understood that when b is other than 0, b is a distribution having a mode equal to a stated value;

wherein at least one $R^1$ comprises a monovalent reactive group, and in some embodiments between one and 3 $R^1$ comprise monovalent reactive groups.

As used herein "monovalent reactive groups" are groups that can undergo free radical and/or cationic polymerization. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl (meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof.

Suitable monovalent alkyl and aryl groups include unsubstituted monovalent $C_1$ to $C_{16}$alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof and the like.

In one embodiment b is zero, one $R^1$ is a monovalent reactive group, and at least 3 $R^1$ are selected from monovalent alkyl groups having one to 16 carbon atoms, and in another embodiment from monovalent alkyl groups having one to 6 carbon atoms. Non-limiting examples of silicone components of this embodiment include 2-methyl-,2-hydroxy-3-[3-[1,3,3,3-tetramethyl-1-[(trimethylsilyl)oxy]disiloxanyl]propoxy]propyl ester ("SiGMA"), 2-hydroxy-3-methacryloxypropyloxypropyl-tris(trimethylsiloxy)silane, 3-methacryloxypropyltris(trimethylsiloxy)silane ("TRIS"), 3-methacryloxypropylbis(trimethylsiloxy)methylsilane and 3-methacryloxypropylpentamethyl disiloxane.

In another embodiment, b is 2 to 20, 3 to 15 or in some embodiments 3 to 10; at least one terminal $R^1$ comprises a monovalent reactive group and the remaining $R^1$ are selected from monovalent alkyl groups having 1 to 16 carbon atoms, and in another embodiment from monovalent alkyl groups having 1 to 6 carbon atoms. In yet another embodiment, b is 3 to 15, one terminal $R^1$ comprises a monovalent reactive group, the other terminal $R^1$ comprises a monovalent alkyl group having 1 to 6 carbon atoms and the remaining $R^1$ comprise monovalent alkyl group having 1 to 3 carbon atoms. Non-limiting examples of silicone components of this embodiment include (mono-(2-hydroxy-3-methacryloxypropyl)-propyl ether terminated polydimethylsiloxane (400-1000 MW)) ("OH-mPDMS"), monomethacryloxypropyl terminated mono-n-butyl terminated polydimethylsiloxanes (800-1000 MW), ("mPDMS").

In another embodiment b is 5 to 400 or from 10 to 300, both terminal $R^1$ comprise monovalent reactive groups and the remaining $R^1$ are independently selected from monovalent alkyl groups having 1 to 18 carbon atoms which may have ether linkages between carbon atoms and may further comprise halogen.

In one embodiment, where a silicone hydrogel lens is desired, the lens of the present invention will be made from a Reactive Mixture comprising at least about 20 and preferably between about 20 and 70% wt silicone containing components based on total weight of reactive monomer components from which the polymer is made.

In another embodiment, one to four $R^1$ comprises a vinyl carbonate or carbamate of the formula:

$$\underset{\text{Formula II}}{H_2C=\overset{R}{\underset{|}{C}}-(CH_2)_q-O-\overset{O}{\underset{\|}{C}}-Y}$$

wherein: Y denotes —O—, —S— or —NH—;
R denotes, hydrogen or methyl; d is 1, 2, 3 or 4; and q is 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio) propyl-[tris(trimethylsiloxy)silane]; 3-[tris(trimethylsiloxy)silyl] propyl allyl carbamate; 3-[tris(trimethylsiloxy)silyl] propyl vinyl carbamate; trimethylsilylethyl vinyl carbonate; trimethylsilylmethyl vinyl carbonate, and $$H_2C=\underset{H}{\overset{O}{\underset{\|}{C}}}-OCO(CH_3)_4-\underset{CH_3}{\overset{CH_3}{\underset{|}{Si}}}-O-\left[\underset{CH_3}{\overset{CH_3}{\underset{|}{Si}}}-O\right]_{25}-\underset{CH_3}{\overset{CH_3}{\underset{|}{Si}}}-(CH_2)_4O\underset{H}{\overset{O}{\underset{\|}{C}}}-C=CH_2$$

Where biomedical devices with modulus below about 200 are desired, only one $R^1$ shall comprise a monovalent reactive group and no more than two of the remaining $R^1$ groups will comprise monovalent siloxane groups.

Another class of silicone-containing components includes polyurethane macromers of the following formulae:

$$(*D*A*D*G)_a*D*D*E^1;$$

$$E(*D*G*D*A)_a*D*G*D*E^1 \text{ or;}$$

$$E(*D*A*D*G)_a*D*A*D*E^1 \qquad \text{Formulae IV-VI}$$

wherein:
D denotes an alkyl diradical, an alkyl cycloalkyl diradical, a cycloalkyl diradical, an aryl diradical or an alkylaryl diradical having 6 to 30 carbon atoms,
G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;
* denotes a urethane or ureido linkage;
$a$ is at least 1;
A denotes a divalent polymeric radical of formula:

$$\underset{\text{Formula VII}}{-(CH_2)_y-\left[\underset{\underset{R^{11}}{|}}{\overset{\overset{R^{11}}{|}}{SiO}}\right]_p-\underset{\underset{R^{11}}{|}}{\overset{\overset{R^{11}}{|}}{Si}}-(CH_2)_y-}$$

$R^{11}$ independently denotes an alkyl or fluoro-substituted alkyl group having 1 to 10 carbon atoms which may contain ether linkages between carbon atoms; y is at least 1; and p provides a moiety weight of 400 to 10,000; each of E and $E^1$ independently denotes a polymerizable unsaturated organic radical represented by formula:

$$\underset{\text{Formula VIII}}{R^{13}CH=\underset{|}{\overset{R^{12}}{C}}-(CH_2)_w-(X)_x-(Z)_z-(Ar)_y-R^{14}-}$$

wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

A preferred silicone-containing component is a polyurethane macromer represented by the following formula:

$$\underset{\text{Formula IX}}{CH_2=\underset{CH_3}{\overset{|}{C}}-\overset{O}{\underset{\|}{C}}OCH_2CH_2\left[OCN-R^{16}-\underset{H}{N}COCH_2CH_2OCH_2CH_2O\underset{H}{C}N-R^{16}-\underset{H}{N}CO(CH_2)_m\left(\underset{CH_3}{\overset{CH_3}{\underset{|}{SiO}}}\right)_p\underset{CH_3}{\overset{CH_3}{\underset{|}{Si}}}-(CH_2)_m\right]_a}$$

$$-O\underset{H}{C}N-R_{16}-\underset{H}{N}COCH_2CH_2OCH_2CH_2O\underset{H}{C}N-R^{16}-\underset{H}{N}CO-CH_2CH_2COO\underset{CH_3}{\overset{CH_3}{\underset{|}{C}}}=CH_2$$

wherein $R^{16}$ is a diradical of a diisocyanate after removal of the isocyanate group, such as the diradical of isophorone diisocyanate. Another suitable silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

Formula X

Other silicone containing components suitable for use in this invention include macromers containing polysiloxane, polyalkylene ether, diisocyanate, polyfluorinated hydrocarbon, polyfluorinated ether and polysaccharide groups; polysiloxanes with a polar fluorinated graft or side group having a hydrogen atom attached to a terminal difluoro-substituted carbon atom; hydrophilic siloxanyl methacrylates containing ether and siloxanyl linkanges and crosslinkable monomers containing polyether and polysiloxanyl groups. Any of the foregoing polysiloxanes can also be used as the silicone-containing component in this invention.

CONCLUSION

The present invention, as described above and as further defined by the claims below, provides for methods and apparatus for manufacturing an Ophthalmic Lens with passive event coloration mechanisms, which may not require a power source. In some embodiments, the passive event coloration mechanisms may be combined with Rigid Inserts or Media Inserts, wherein the inserts may provide additional functionalities.

The invention claimed is:

1. A method of manufacturing an ophthalmic lens with an event coloration mechanism, the method comprising the steps of:
    providing a front curve mold part and a back curve mold part, each having an optic zone portion and a peripheral edge portion surrounding the optic zone portion;
    introducing an event coloration mechanism in proximity to the optic zone portion of one or both of the front curve mold part and the back curve mold part wherein the event coloration mechanism is capable of triggering a visual indication in an optic zone of the ophthalmic lens as to be visible to a wearer, based on an occurrence of a predefined event occurring while the ophthalmic lens is in the eye of the wearer; and wherein the event coloration mechanism comprises:
        a first reservoir containing a first substance that is capable of coloration by reacting with a predefined constituent or a predefined condition of a tear fluid of an eye, wherein the predefined constituent or the predefined condition is indicative of the predefined event; and
        an encapsulating layer encapsulating the first reservoir;
    adding a reactive monomer mixture to one or both of the front curve mold part and the back curve mold part;
    placing the back curve mold part proximate to the front curve mold part;
    curing the reactive monomer mixture to form the ophthalmic lens;
    demolding the front curve mold part and the back curve mold part; and
    removing the ophthalmic lens from the demolded front curve mold part and back curve mold part.

2. The method of claim 1, further comprising the step of hydrating the ophthalmic lens.

3. The method of claim 1, wherein the event coloration mechanism further comprises a rigid insert.

4. The method of claim 1, wherein the introduction of the event coloration mechanism occurs prior to curing, and comprises mixing the event coloration mechanism with the reactive monomer mixture.

5. The method of claim 2, wherein the predefined event comprises a predefined pH level.

6. The method of claim 1, wherein the event coloration mechanism comprises liquid crystal, wherein the liquid crystal is capable of altering color based on a temperature change in the ocular environment.

7. The method of claim 1, wherein the encapsulating occurs after the curing, and the encapsulating further comprises the method steps of: injecting the event mechanism into the lens at a predefined depth.

8. The method of claim 1, wherein the introduction of the event coloration mechanism occurs before the curing, and comprises injecting the event coloration mechanism into a location that will be between the front curve mold part and the back curve mold part, wherein the curing of the reactive monomer mixture is capable of securing the event coloration mechanism within the lens.

9. The method of claim 1, wherein the encapsulating layer is selectively permeable to the predefined constituent.

10. The method of claim 3, wherein the introduction of the event coloration mechanism occurs prior to curing, and comprises placing the event coloration mechanism in a location that will be between the front curve mold part and the back curve part.

11. The method of claim 3, wherein the encapsulating occurs after the curing, and the encapsulating further comprises the method steps of: inserting the event coloration mechanism into the lens.

12. The method of claim 3, wherein the encapsulating occurs after the curing, and the encapsulating further comprises the method steps of: inserting the event coloration mechanism into the lens.

13. The method of claim 4, further comprising the method steps of: curing the event coloration mechanism.

14. The method of claim 8, wherein the curing is capable of curing the encapsulating layer of the event coloration mechanism.

15. The method of claim 12, wherein the curing of the event coloration mechanism comprises a separate curing process than the curing of the Reactive Monomer Mixture.

16. The method of claim 12, wherein at least a portion of the curing of the event coloration mechanism and at least a portion of the curing of the Reactive Monomer Mixture occur simultaneously.

17. A method of manufacturing an ophthalmic lens with an event coloration mechanism, the method comprising the steps of:
    providing a front curve mold part and a back curve mold part, each having an optic zone portion and a peripheral edge portion surrounding the optic zone portion;
    introducing an event coloration mechanism in proximity to the optic zone portion of one or both of the front curve mold part and the back curve mold part wherein the event coloration mechanism is capable of triggering a visual indication in an optic zone of the ophthalmic lens as to be visible to a wearer, based on an occurrence of a predefined event occurring while the ophthalmic lens is in the eye of the wearer; and wherein the event coloration mechanism comprises a reactive molecule capable of coloration by binding to a predefined constituent of a tear fluid of an eye that is indicative of the predefined event, said reactive molecule comprising:
    a binding portion capable of binding with the predefined constituent, wherein the binding is capable of altering a configuration of the reactive molecule, and wherein a change in configuration is capable of providing the visual indication;
    an acceptor coloration portion located on a first end of the binding portion; and
    a donor coloration portion located on a second end of the binding portion;
    adding a reactive monomer mixture to one or both of the front curve mold part and the back curve mold part;
    placing the back curve mold part proximate to the front curve mold part;
    curing the reactive monomer mixture to form the ophthalmic lens;
    demolding the front curve mold part and the back curve mold part; and
    removing the ophthalmic lens from the demolded front curve mold part and back curve mold part.

18. The method of claim 1, wherein the event coloration mechanism is not visible to the wearer of the ophthalmic lens in an absence of the predefined event occurring.

19. The method of claim 1, wherein at least a portion of the event coloration mechanism that is capable of triggering the visual indication is outside of the line of sight of the wearer of the ophthalmic lens in an absence of the predefined event occurring.

20. The method of claim 17, wherein the event coloration mechanism is not visible to the wearer of the ophthalmic lens in an absence of the predefined event occurring.

* * * * *